(12) United States Patent
Komori

(10) Patent No.: US 8,758,997 B2
(45) Date of Patent: Jun. 24, 2014

(54) METHOD FOR DETECTING POLYMORPHISM AT NUCLEOTIDE POSITION-1639 OF VKORC1 GENE, AND NUCLEIC ACID PROBE AND KIT THEREFOR

(75) Inventor: Mariko Komori, Kyoto (JP)

(73) Assignee: Arkray, Inc., Kyoto (JP)

( * ) Notice: Subject to any disclaimer, the term of this patent is extended or adjusted under 35 U.S.C. 154(b) by 332 days.

(21) Appl. No.: 13/150,680

(22) Filed: Jun. 1, 2011

(65) Prior Publication Data

US 2011/0300539 A1 Dec. 8, 2011

(30) Foreign Application Priority Data

Jun. 1, 2010 (JP) .................................. 2010-126306

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ......... 435/6.1; 435/91.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 6,699,661 B1 | 3/2004 | Kurane | |
| 7,354,707 B2 | 4/2008 | Kurane | |
| 8,232,051 B2 * | 7/2012 | Hirai et al. ..................... | 435/6.1 |
| 2009/0233288 A1 | 9/2009 | Hirai | |

FOREIGN PATENT DOCUMENTS

| | | | |
|---|---|---|---|
| CN | 101886117 A | 11/2010 | |
| EP | 2 128 273 A1 | 12/2009 | |
| JP | 2001-286300 A | 10/2001 | |
| JP | 2002-119291 A | 4/2002 | |
| JP | 2009-219445 A | 10/2009 | |
| WO | 2006/069339 A2 | 6/2006 | |
| WO | 2007/143617 A1 | 12/2007 | |
| WO | 2008/117782 A1 | 10/2008 | |
| WO | WO2008/117782 | * 10/2008 | .................... 435/601 |

OTHER PUBLICATIONS

Gage, Brian F. Hematology, 2006, pp. 467-473.*
NCBI, National Library or Medicine, dbSNP rs9923231, 2003.*
Joshi et al., "Platform evaluation for rapid genotyping of CYP2C9 and VKORC1 alleles," Personalized Medicine, 6: 449-457 (2009).
Carlquist et al. (2008) Rapid melting curve analysis for genetic variants that underlie inter-individual variability in stable warfarin dosing, J. Thromb. Thrombolysis, 26:1-7.
Lyon et al. (2008) Pharmacogenetic testing for Warfarin sensitivity, Clin. Lab. Med., 28:525-537.
McKinney et al. (2009) CYP2C9 and VKORC1 genotyping reagents from Idaho Technology: rapid turn-around, accurate results, Nat. Methods, Jul.: v-vi.
European Patent Application No. 11168544.2 Extended European Search Report dated Nov. 2, 2011.
Mcclain et al. A Rapid-ACCE Review of CYP2C9 and VKORC1 Alleles Testing to Inform Warfarin Dosing in Adults at Elevated Risk for Thrombotic Events to Avoid Serious Bleeding, Genetics in Medicine, vol. 10, pp. 89-98, 2008.
Millican et al. Genetic-Based Dosing in Orthopedic Patients Beginning Warfarin Therapy, Blood, vol. 110, pp. 1511-1515, 2007.
Nonen et al. Impact of Genetic Polymorphism on Maintenance Dose of Warfarin; a Case Report of the Patient with High Dose, TDM Research, vol. 25, pp. 141-144, 2008.
Rieder et al. Effect of VKORC1 Haplotypes on Transcriptional Regulation and Warfarin Dose, The New England Journal of Medicine, vol. 352, pp. 2285-2293, 2005.
Rost et al. Mutations in VKORC1 Cause Warfarin Resistance and Multiple Coagulation Factor Deficiency Type 2, Nature, vol. 427, pp. 537-544, 2004.

* cited by examiner

*Primary Examiner* — Jehanne Sitton
(74) *Attorney, Agent, or Firm* — Morgan, Lewis & Bockius LLP

(57) ABSTRACT

A probe for detecting a polymorphism at position −1639 of the VKORC1 gene, the probe comprising an oligonucleotide having a nucleotide sequence having a length of 10 to 50 nucleotides, which nucleotide sequence comprises the nucleotides 80 to 89 of SEQ ID NO:1 or 2 and has a homology to SEQ ID NO:1 or 2 except that the nucleotide corresponding to the nucleotide at position 80 in SEQ ID NO:1 or 2 is cytosine, which nucleotide corresponding to the nucleotide at position 80 is labeled with a fluorescent dye.

8 Claims, 7 Drawing Sheets

SEQUENCE LISTING

```
<160> NUMBER OF SEQ ID NOS: 10

<210> SEQ ID NO 1
<211> LENGTH: 180
<212> TYPE: DNA
<213> ORGANISM: Homo sapiens

<400> SEQUENCE: 1
aagagagttc ccagaagggt aggtgcaaca gtaagggatc cctctgggaa gtcaagcaag      60
agaagacctg aaaaacaacc attggccggg tgcggtggct cacgcctata atcctagcat    120
tttgggaggc cgaggtgggt ggatcacttg aggtcaggag tttaagacaa gcctggccaa    180

<210> SEQ ID NO 2
<211> LENGTH: 180
<212> TYPE: DNA
<213> ORGANISM: Homo sapiens

<400> SEQUENCE: 2
aagagagttc ccagaagggt aggtgcaaca gtaagggatc cctctgggaa gtcaagcaag      60
agaagacctg aaaaacaacc attggccagg tgcggtggct cacgcctata atcctagcat    120
tttgggaggc cgaggtgggt ggatcacttg aggtcaggag tttaagacaa gcctggccaa    180

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ggaagtcaag caagagaaga cctg                                             24

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
aatgctagga ttataggcgt gag                                              23

<210> SEQ ID NO 5
<211> LENGTH: 17
<212> TYPE: DNA
<213> ORGANISM: Artificial Sequence
<220> FEATURE:
<223> OTHER INFORMATION: probe

<400> SEQUENCE: 5
cattggccrg gtgcggt                                                     17

<210> SEQ ID NO 6
<211> LENGTH: 17
<212> TYPE: DNA
<213> ORGANISM: Artificial Sequence
<220> FEATURE:
<223> OTHER INFORMATION: probe

<400> SEQUENCE: 6
cattggccag gtgcggt                                                     17
```

-continued

```
<210> SEQ ID NO 7
<211> LENGTH: 16
<212> TYPE: DNA
<213> ORGANISM: Artificial Sequence
<220> FEATURE:
<223> OTHER INFORMATION: probe

<400> SEQUENCE: 7
cacctggcca atggtt                                                     16

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
cggagcccct gcatgcaa                                                   18

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
aatgatacta tgaatttggg gacttcgaa                                       29

<210> SEQ ID NO 10
<211> LENGTH: 18
<212> TYPE: DNA
<213> ORGANISM: Artificial Sequence
<220> FEATURE:
<223> OTHER INFORMATION: probe

<400> SEQUENCE: 10
ggagaaggtc aaggtatc                                                   18
```

METHOD FOR DETECTING POLYMORPHISM AT NUCLEOTIDE POSITION-1639 OF VKORC1 GENE, AND NUCLEIC ACID PROBE AND KIT THEREFOR

RELATED APPLICATIONS

This application claims priority to Japanese Application No. 2010-126306, filed Jun. 1, 2010; which is hereby incorporated by reference in its entirety.

SEQUENCE LISTING SUBMISSION VIA EFS-WEB

A computer readable text file, entitled "068022-5114-SequenceListing.txt" created on or about Jun. 1, 2011 with a file size of about 3 kb contains the sequence listing for this application and is hereby incorporated by reference in its entirety.

TECHNICAL FIELD

The present invention relates to a method for detecting a polymorphism at position −1639 of the VKORC1 gene, and a nucleic acid probe and a kit therefor.

As a drug for preventing coagulation of blood in a patient suffering from myocardial infarction or cerebral infarction, warfarin has been widely used. The optimal dose of warfarin largely varies among different human races, and, even in the same human race, individual differences are observed. High-dose administration of warfarin may cause epistaxis or subcutaneous hemorrhage, or, in some cases, side effects such as intracerebral hemorrhage. Therefore, it is very important to determine the optimal dose of warfarin for each patient when the treatment is carried out.

In terms of determination of such an optimal dose of warfarin, it has been recently reported that polymorphisms of the CYP2C9 gene and the VKORC1 gene influence the pharmacological effect of warfarin (Simone Rost et al., Nature Vol. 427 2004 letters to nature and Mark J. Rieder et al., The New England Journal of Medicine 352; 22, 2005). The CYP2C9 gene is a gene that encodes cytochrome P450, which produces a warfarin metabolic enzyme. The VKORC1 gene is a gene that encodes a protein which acts on vitamin K, which is involved in coagulation of blood. Therefore, detection of polymorphisms of these two genes is very important for determining the optimal dose of warfarin depending on the patient, to reduce side effects. Known examples of the polymorphism of the VKORC1 gene include 1173C>T (rs9934438) and −1639 G>A (rs9923231). Such polymorphisms of the VKORC1 gene are described in TDM Research Vol. 25 No. 4 (2008) 141-144, BLOOD, 1 Sep. 2007 VOLUME 110, NUMBER 5, and Genet Med. 2008 February; 10(2): 89-98.

Examples of the method for detecting polymorphisms of a nucleotide include the PCR-RFLP method (TDM Research Vol. 25 No. 4 (2008) 141-144) and the method by detecting a mutation by pyrosequencing (BLOOD, 1 Sep. 2007 VOLUME 110, NUMBER 5).

However, the PCR-RFLP method in TDM Research Vol. 25 No. 4 (2008) 141-144 requires much labor and cost since, for example, the method needs extraction and purification of DNA and PCR, followed by restriction enzyme treatment of the amplified product and then electrophoresis. Further, since treatment of the amplified product is necessary after the PCR, there is a risk of contamination of the amplified product to the subsequent reaction system; automation is difficult; and testing of plural nucleic acid sequences at the same time is impossible; which have been problematic.

The pyrosequencing in BLOOD, 1 Sep. 2007 VOLUME 110, NUMBER 5 is based on the principle that, by converting pyrophosphoric acid, which is released upon incorporation of a nucleotide into DNA, to ATP and using it for luminescent reaction, the amount of the nucleotide incorporated into the DNA can be quantified. Practically, by repeating a process in which one each type of deoxyribonucleotide is added and the amount of luminescence is measured, followed by removing the deoxyribonucleotide, the sequence is determined. For removal of the excess nucleotide, there is the solid-phase method, in which the template DNA is bound to a certain solid-phase substrate and the reaction liquid is removed by washing, and the liquid-phase method, in which the nucleotide is decomposed by addition of apyrase. Although a system for automatically carrying out such complicated operations is commercially available, they are very expensive and costly. Further, there are problems such as requirement of extraction and purification of DNA and pretreatment, which require much labor and cost.

On the other hand, there is a known method in which a region containing a mutation is amplified by PCR and melting curve analysis is then carried out using a nucleic acid probe labeled with a fluorescent dye, followed by analyzing the mutation based on the result of the melting curve analysis (JP 2001-286300 A and JP 2002-119291 A). However, these literatures only teach that the probe is designed such that, when a quenching probe labeled at its end with a fluorescent dye is hybridized to the target nucleic acid, plural base pairs of the probe-nucleic acid hybrid form at least one GC pair at the end portion.

In WO2008/117782, a method is described in which melting curve analysis is carried out using a probe whose 5′-end is fluorescently labeled, to detect VKORC1 1173C>T (rs9934438) and CYP2C9*3 at the same time. However, there is no description of a method to detect the polymorphism VKORC1−1639 G>A (rs9923231). Further, there is no description of a method to detect the polymorphism VKORC1−1639 G>A (rs9923231) and a polymorphism at the CYP2C9*3 mutation site at the same time.

SUMMARY OF THE INVENTION

The present invention aims to specify a quenching probe effective for detecting a polymorphism at position −1639 of the VKORC1 gene and to provide a method for detecting the polymorphism at position −1639 of the VKORC1 gene and a kit therefor.

The present inventors discovered that, by designing a quenching probe based on a particular region containing a polymorphism at position −1639 of the VKORC1 gene and carrying out melting curve analysis using the quenching probe, the mutation can be detected, thereby completing the present invention.

That is, the present invention is as follows.
(1) A probe for detecting a polymorphism of the nucleotide at position −1639 of the VKORC1 gene, said probe comprising an oligonucleotide having a nucleotide sequence having a length of 10 to 50 nucleotides, which nucleotide sequence comprises the nucleotides 80 to 89 of SEQ ID NO:1 or 2 and has a homology to SEQ ID NO:1 or 2 except that the nucleotide corresponding to the nucleotide at position 80 in SEQ ID NO:1 or 2 is cytosine, which nucleotide corresponding to the nucleotide at position 80 is labeled with a fluorescent dye.

(2) The probe according to (1), wherein said oligonucleotide has the nucleotide corresponding to the nucleotide at position 80 labeled with a fluorescent dye, at the first, second or third position from the 5'-end.
(3) The probe according to (1), said probe having the nucleotide corresponding to the nucleotide at position 80 labeled with a fluorescent dye, at the 5'-end.
(4) The probe according to (1), wherein said oligonucleotide emits fluorescence when the oligonucleotide is not hybridized with a target sequence, and the fluorescence intensity decreases or increases when the oligonucleotide is hybridized with the target sequence.
(5) The probe according to (4), wherein said oligonucleotide emits fluorescence when the oligonucleotide is not hybridized with a target sequence, and the fluorescence intensity decreases when the oligonucleotide is hybridized with the target sequence.
(6) The probe according to (1), wherein said oligonucleotide has a length of 10 to 40 nucleotides.
(7) The probe according to (1), wherein said oligonucleotide has a length of 15 to 30 nucleotides.
(8) The probe according to (1), wherein said oligonucleotide has a length of 15 to 25 nucleotides.
(9) The probe according to (1), wherein said probe is a probe for melting curve analysis.
(10) The probe according to (1), wherein said oligonucleotide consists of the nucleotide sequence of SEQ ID NO:6.
(11) A method for detecting a polymorphism in the VKORC1 gene, which method comprises using the probe according to (1).
(12) The method according to (11), said method comprising:
(I) bringing the probe according to (1) into contact with a single-stranded nucleic acid in a sample, to allow hybridization of said fluorescently labeled oligonucleotide with said single-stranded nucleic acid;
(II) changing the temperature of the sample containing the hybrid to dissociate the hybrid, and measuring fluctuation of the fluorescence signal due to the dissociation of the hybrid;
(III) determining the Tm value, which is the dissociation temperature of the hybrid, based on the fluctuation of said signal; and
(IV) determining the presence of a polymorphism or the abundance ratios of nucleic acids having polymorphisms in the VKORC1 gene based on said Tm value.
(13) The method according to (12), said method further comprising amplification of nucleic acid before said Step (I) or at the same time with said Step (I).
(14) A method for judging the optimal dose of warfarin, said method comprising detecting a polymorphism in the VKORC1 gene by the method according to (11), and judging the optimal dose of warfarin based on the detected presence/absence of the polymorphism.
(15) A kit for detecting a polymorphism, said kit comprising the probe according to (1).
(16) The kit according to (15), further comprising a primer(s) for amplification of a region in the nucleotide sequence shown in SEQ ID NO:1, said region comprising a sequence with which said oligonucleotide hybridizes.
(17) The kit according to (16), wherein said primers are the primers shown in SEQ ID NOs:3 and 4.
(18) The kit according to (16), further comprising the primers shown in SEQ ID NOs:8 and 9 and the probe shown in SEQ ID NO:10.

By adding the probe of the present invention to the gene amplification system in advance, typing of plural gene variants is possible by just carrying out melting curve analysis (Tm analysis) after finishing the PCR reaction. Further, since direct testing of whole blood and oral mucosal suspensions is possible, the labor and the cost can be reduced.

The probe of the present invention has a high specificity and a high detection sensitivity.

By using the method of the present invention, even in cases where PCR is carried out, the amplification product does not need to be removed, so that there is hardly a risk of contamination. Further, since the method of the present invention has a simple mechanism, its automation can be easily attained.

By the method of the present invention, a polymorphism at position −1639 of the VKORC1 gene and a polymorphism at the CYP2C9*3 mutation site can be detected at the same time.

DESCRIPTION OF THE PREFERRED EMBODIMENTS

Figure 1:
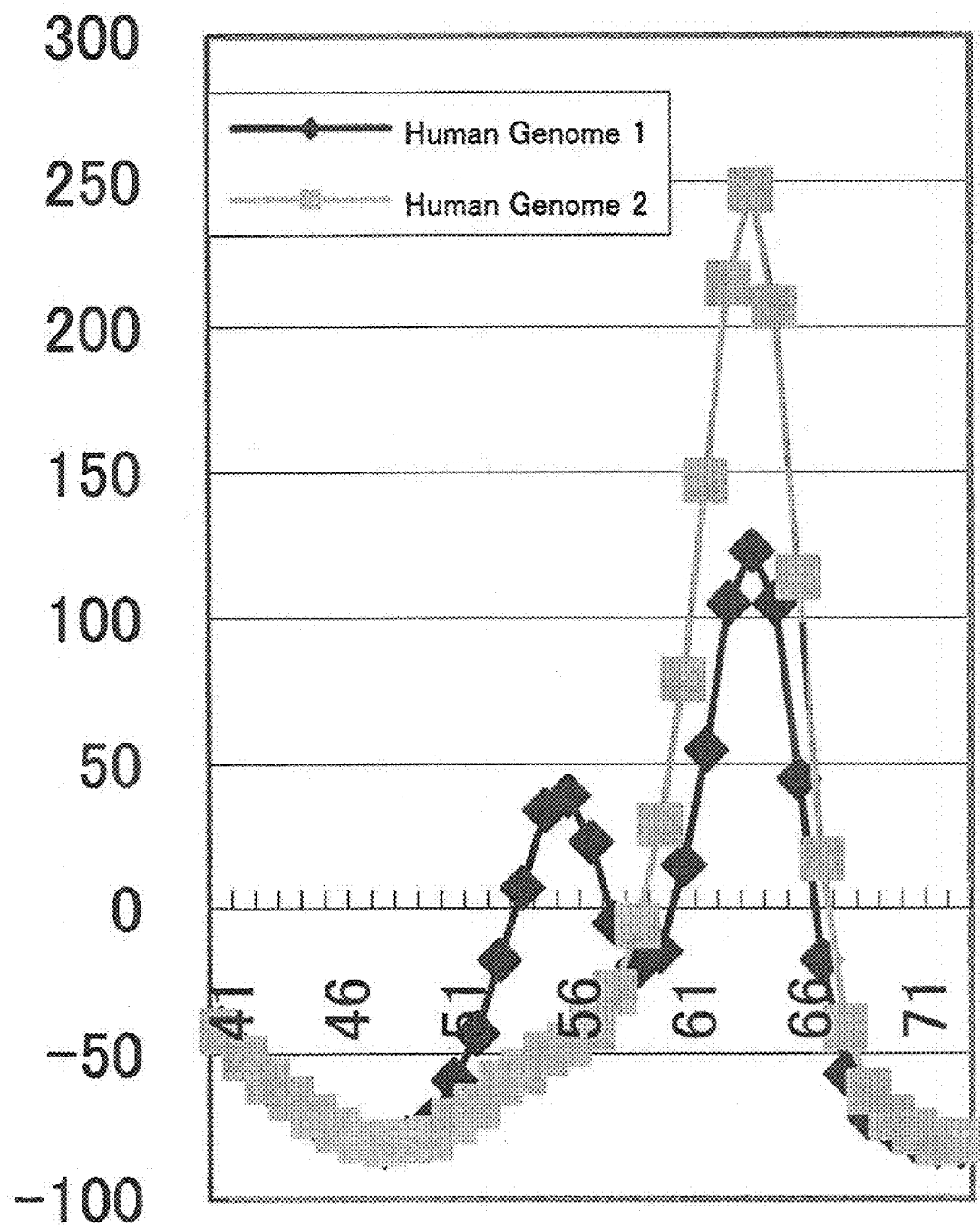
FIG. 1 shows the changes in the amount of change in the fluorescence intensity of TAMRA (VKORC1 probe 1) per unit time (d the amount of increase in the fluorescence intensity/t) in Tm analysis for the human genome 1 and the human genome 2 (purified genome) in Example 1. The ordinate indicates the amount of change in the fluorescence intensity per unit time (d the amount of increase in the fluorescence intensity/t), and the abscissa indicates the temperature (° C.).

<1> Probe and Detection Method of the Present Invention

The probe of the present invention is a probe for detecting a polymorphism of the nucleotide at position −1639 of the VKORC1 gene, the probe comprising an oligonucleotide having a nucleotide sequence having a length of 10 to 50 nucleotides, which nucleotide sequence comprises the nucleotides 80 to 89 of SEQ ID NO:1 or 2 and has a homology to SEQ ID NO:1 or 2 except that the nucleotide corresponding to the nucleotide at position 80 of SEQ ID NO:1 or 2 is cytosine, which nucleotide corresponding to the nucleotide at position 80 is labeled with a fluorescent dye. Here, the nucleotide at position −1639 of the VKORC1 gene is the nucleotide at position 88 in SEQ ID NO:1 or 2.

The probe of the present invention can be prepared in the same manner as the quenching probes described in JP 2001-286300 A and JP 2002-119291 A except that the probe of the present invention has the above-described specified sequence in the nucleotide sequence shown in SEQ ID NO:1 (sequence having the wild-type nucleotide at position −1639 of the VKORC1 gene) or the nucleotide sequence shown in SEQ ID NO:2 (sequence having a variant (polymorphic) nucleotide at position −1639 of the VKORC1 gene). The sequence of the present invention shown in SEQ ID NO:1 corresponds to positions 3501 to 3680 of GenBank Accession No. NG_011564. The length of the probe of the present invention is 10 to 50 nucleotides, preferably 10 to 40 nucleotides, more preferably 15 to 30 nucleotides, most preferably 15 to 25 nucleotides.

Examples of the nucleotide sequence of the probe used in the present invention include 5'-cattggccrggtgcggt-3' (SEQ ID NO:5). In the sequence, "r" represents a or g. The nucleotide sequence is more preferably 5'-cattggccaggtgcggt-3' (SEQ ID NO:6).

As the fluorescent dye, those described in JP 2001-286300 A and JP 2002-119291 A may be used, and particular examples thereof include Pacific Blue (trademark), FAM (trademark), TAMRA (trademark) and BODIPY (trademark) FL. The method of linking of the fluorescent dye to the oligonucleotide may be carried out according to a conventional method, such as the one described in JP 2001-286300 A and JP 2002-119291 A.

The term "homology" herein means a nucleotide sequence having a sequence having a homology of not less than 80%, more preferably not less than 90%, most preferably 95% to a nucleotide sequence in a particular nucleotide sequence. That is, the probe of the present invention has a sequence homologous to a nucleotide sequence having a length of 10 to 50 nucleotides containing the nucleotides 80 to 89 of SEQ ID NO:1 or 2, but these sequences do not need to be completely identical, and only 5 nucleotides, 4 nucleotides, 3 nucleotides, 2 nucleotides or 1 nucleotide may be different therebetween.

Fluorescence of the fluorescent dye of the probe of the present invention preferably decreases or increases when the probe is hybridized with a target sequence. The probe of the present invention is preferably a quenching probe, wherein fluorescence of the fluorescent dye is quenched upon hybridization.

Further, the probe of the present invention is preferably labeled at 5' or 3' with a fluorescent dye.

In the present specification, when the term "first, second or third position from the 5'-end" is mentioned, the 5'-end is counted as the first position, and, when the term "first, second or third position from the 3'-end" is mentioned, the 3'-end is counted as the first position As shown in Table 2 in Examples of the present invention, by using the oligonucleotide of SEQ ID NO:6, a polymorphism at position −1639 of the VKORC1 gene can be detected.

The detection method of the present invention is a method wherein a nucleic acid having the polymorphic site at position −1639 of the VKORC1 gene is subjected to melting curve analysis by using a nucleic acid probe labeled with a fluorescent dye and measuring fluorescence of the fluorescent dye, to detect the polymorphism based on the result of the melting curve analysis, which nucleic acid probe is the probe of the present invention.

The detection method of the present invention can be carried out according to conventional methods for nucleic acid amplification and melting curve analysis (Tm analysis) except that a region containing the polymorphic site at position −1639 of the VKORC1 gene is amplified and that the probe of the present invention is used.

The detection method of the present invention preferably uses the probe of the present invention and comprises the following steps:

(I) the step of adding the probe of the present invention to a sample containing DNA and allowing the probe to hybridize with the DNA;

(II) the step of dissociating the hybrid between the probe and the target DNA by changing the temperature, and measuring fluctuation of the signal due to the dissociation of the hybrid;

(III) the step of determining the Tm value by analyzing the fluctuation of the signal; and (IV) the step of determining the presence/absence of the polymorphism of interest or the abundance ratios of nucleotide sequences having polymorphisms.

The detection method of the present invention may be carried out according to conventional methods for nucleic acid amplification and melting curve analysis (Tm analysis) except that the probe of the present invention is used. Further, the detection method of the present invention may comprise amplification of nucleic acid before the Step (I) or at the same time with the Step (I).

The method of nucleic acid amplification is preferably a method using a polymerase, and examples thereof include PCR, ICAN and LAMP. In cases where the amplification is carried out by a method using a polymerase, the amplification is preferably carried out in the presence of the probe of the present invention. Those skilled in the art can easily adjust the reaction conditions and the like of the amplification depending on the probe used. Since, by this, the detection can be carried out just by analyzing the Tm value of the probe after the nucleic acid amplification, there is no need to handle the amplified product after the reaction. Therefore, the risk of contamination by the amplified product can be avoided. Further, since the detection can be carried out using the same instrument as the one necessary for the amplification, there is no need even to transfer the container. Thus, automation can be attained easily.

In the present invention, the DNA in the sample may be either a single-stranded DNA or a double-stranded DNA. In cases where the DNA is a double-stranded DNA, for example, a step of dissociating the double-stranded DNA in the sample by heating is preferably included before the hybridization step. By dissociating the double-stranded DNA into single-stranded DNAs, hybridization with the detection probe is possible in the subsequent hybridization step.

In the present invention, the ratio (molar ratio) of the probe of the present invention to be added with respect to DNA in the sample is not restricted, and the ratio is preferably not more than 1, more preferably not more than 0.3 with respect to DNA in the sample in view of securing a sufficient detection signal. In this case, for example, the DNA in the sample may be either the total of the DNA comprising a polymorphism to be detected and DNA which does not comprise the polymorphism to be detected, or the total of the amplification product containing the sequence comprising a polymorphism to be detected and amplification products containing sequences which do not comprise the polymorphism to be detected. Although the ratio of the DNA to be detected in the DNA in the sample is usually not known, the ratio (molar ratio) of the probe to be added with respect to the DNA to be detected (the amplification product containing the sequence to be detected) is preferably not more than 100, more preferably not more than 50, still more preferably not more than 30 as a result. The lower limit of the ratio is not restricted, and the ratio is, for example, not less than 0.001, preferably not less than 0.01, more preferably not less than 0.2.

The ratio of the probe of the present invention to be added with respect to the DNA may be, for example, either a molar ratio with respect to the double-stranded DNA or a molar ratio with respect to the single-stranded DNA.

The Tm value will now be described. Heating a solution containing double-stranded DNA causes increase in the absorbance at 260 nm. This is caused because the hydrogen bond between the both strands of the double-stranded DNA is unraveled by the heat and the double-stranded DNA is dissociated into single-stranded DNAs (melting of DNA). When all the double-stranded DNAs are dissociated into single-stranded DNAs, the absorbance becomes about 1.5 times as large as that observed when the heating was initiated (absorbance for only double-stranded DNA), and by this, completion of the melting can be judged. Based on this phenomenon, the melting temperature Tm is defined as the temperature at which increase in the absorbance reached 50% of the total increase in the absorbance.

In the present invention, measurement of the signal fluctuation due to the temperature change for determination of the Tm value can be carried out also by measuring the absorbance at 260 nm based on the above-mentioned principle, but the measurement is preferably carried out based on a signal from the label added to the probe of the present invention, which signal fluctuates depending on the state of hybrid formation between the DNA and the probe. Therefore, as the probe of the present invention, the above-mentioned labeled probe is preferably used. Examples of the labeled probe include a fluorescently labeled oligonucleotide probe wherein the probe emits fluorescence when it is not hybridized with the target sequence and the fluorescence intensity decreases (the fluorescence is quenched) when the probe is hybridized with the target sequence, and a fluorescently labeled oligonucleotide probe wherein the probe emits fluorescence when it is not hybridized with the target sequence and the fluorescence intensity increases when the probe is hybridized with the target sequence. In the case of the former probe, the probe shows no signal or a weak signal when it is forming a hybrid (double-stranded DNA) with the sequence to be detected, while the probe shows a signal or the signal increases when the probe is released by heating. In the case of the latter probe, the probe shows a signal by forming a hybrid (double-stranded DNA) with the sequence to be detected, while the signal decreases (disappears) when the probe is released by heating. Therefore, by detecting the change in the signal due to the label under conditions specific to the signal (absorbance and the like), the progress of melting and the determination of Tm value can be carried out similarly to the case of the measurement of the absorbance at 260 nm. For example, the labeling substance in the labeled probe is as mentioned above, and the probe is preferably a fluorescent dye-labeled probe.

The nucleic acid to be used as the template for carrying out the nucleic acid amplification is not restricted as long as it contains a nucleic acid, and examples thereof include those derived from, or those which may be derived from, arbitrary biological origins such as blood; oral mucosal suspensions; somatic cells of nails, hairs and the like; germ cells; milks; ascitic fluids; paraffin-embedded tissues; gastric juices; fluids obtained by gastric lavage; peritoneal fluids; amniotic fluids; and cell cultures. The nucleic acid as the template may be used as it is directly after being obtained from the origin, or may be pretreated to modify the properties of the sample before being used.

The method of nucleic acid amplification is further described by way of an example using PCR. The primer pair used in the PCR may be designed in the same manner as in the method for designing a primer pair for conventional PCR, except that the primer pair is designed such that a region with which the probe of the present invention can hybridize is amplified. The length and the Tm value of each primer is usually 12 mer to 40 mer and 40 to 70° C., preferably 16 mer to 30 mer and 55 to 60° C. The lengths of the respective primers of the primer pair may be different, but the Tm values of the both primers are preferably almost the same (the difference is usually not more than 2° C.). The Tm value is a value calculated by the Nearest Neighbor method. Examples of the primer pair include the one composed of the primers having the nucleotide sequences shown in SEQ ID NOs:3 and 4.

The PCR is preferably carried out in the presence of the probe of the present invention used in the present invention. By this, the Tm analysis can be carried out without handling the amplified product after the amplification reaction. Those skilled in the art can easily adjust the Tm values of the primers and the reaction conditions for the PCR depending on the probe used.

The following is a representative composition of the PCR reaction liquid.

TABLE 1

| DNA fragment | $10^1$ to $10^8$ molecules/reaction |
|---|---|
| Primer | 200 to 1000 nM |
| Probe | 100 to 1000 nM |
| Nucleotide | 20 to 200 μM each |
| DNA polymerase | 0.01 to 0.03 U/μl |
| Tris-HCl (pH 8.4-9.0) | 5 to 25 mM |
| $MgCl_2$ | 1.5 to 3 mM |
| KCl | 10 to 100 mM |
| Glycerol | 0 to 20% |

(Final liquid volume: 10 to 100 μl)

The following is a representative temperature cycle, which is usually repeated 25 to 50 times.
(1) Denaturation, at 90 to 98° C., for 1 to 60 seconds
(2) Annealing, at 50 to 70° C., for 10 to 60 seconds
(3) Extension, at 60 to 75° C., 10 to 180 seconds In cases where the annealing and the extension are carried out as a single step, the conditions are 55 to 70° C. for 10 to 180 seconds, for example.

The Tm analysis may be carried out in the same manner as in a conventional method except that fluorescence of the fluorescent dye of the probe of the present invention is measured. The measurement of fluorescence may be carried out by using excitation light having a wavelength which varies depending on the fluorescent dye and measuring light having an emission wavelength. The heating rate in the Tm analysis is usually 0.1 to 1° C./second. The composition of the reaction liquid used for carrying out the Tm analysis is not restricted as long as the probe can be hybridized with a nucleic acid having the complementary sequence of the nucleotide sequence of the probe, and usually, the concentration of monovalent cations is 1.5 to 5 mM, and the pH is 7 to 9. Since a reaction liquid for an amplification method using a DNA polymerase, such as PCR, usually satisfies these conditions, the reaction liquid after the amplification can be used as it is for the Tm analysis.

Detection of a polymorphism at position −1639 of the VKORC1 gene based on the result of the Tm analysis can be carried out according to a conventional method. The detection in the present invention includes detection of the presence/absence of a mutation.

Since detection of the presence/absence of a mutation is possible by the probe and the method of the present invention, judgment of the optimal dose of warfarin is also included in the present invention. More particularly, in cases where the nucleotide at position −1639 of the VKORC1 gene is A, the sensitivity to warfarin is high, so that reduction of the required dose is suggested. Further, by the method of the present invention, it is also possible to detect a polymorphism at position −1639 of the VKORC1 gene and a polymorphism at the CYP2C9*3 mutation site at the same time. Also in cases where a mutation of CYP2C9*3 exists, the sensitivity to warfarin is high, so that reduction of the required dose is suggested.

The gene sequence of CYP2C9*3, which is a polymorphism of CYP2C9, and the nucleotide sequence of a probe with which a polymorphism of the mutation site can be detected are described in, for example, WO2008/066163 and WO2008/117782. More particularly, the probe is a nucleic acid probe labeled at its 3'-end with a fluorescent dye whose fluorescence decreases upon hybridization, which nucleic acid probe has the nucleotide sequence shown in SEQ ID NO:28 or 29 in WO2008/066163 (SEQ ID NO:44 or 45 in WO2008/117782).

Examples of the probe of the present invention, with which the polymorphism of the VKORC1 gene and the polymorphism at the CYP2C9*3 mutation site can be detected at the same time (that is, detected in a single system) include the nucleic acid probes described in the above-described WO2008/066163 and WO2008/117782.

<2> Kit of Present Invention

The kit of the present invention is a kit to be used in the detection method of the present invention. This kit comprises a nucleic acid probe labeled with a fluorescent dye whose fluorescence changes upon hybridization (quenching probe, preferably), which nucleic acid probe comprises the above-described oligonucleotide. The kit of the present invention can also be used for judging the optimal dose of warfarin.

The probe is as described above for the probe of the present invention.

The detection kit of the present invention may further comprise, in addition to the probe, reagents necessary for amplification of nucleic acid in the detection method of the present invention, especially a primer(s) for amplification using a DNA polymerase.

The probe, primer and other reagents may be contained separately, or a part of these may be contained as a mixture(s).

The present invention will now be described more concretely by way of Examples below.

EXAMPLES

Example 1

Single, Purified Genome

Based on the nucleotide sequence including the polymorphic site at position −1639 of the VKORC1 gene (SEQ ID NO:1 (wild type)), the primers shown in Table 2 were designed such that the polymorphic site can be amplified. In table 2, the positions of the F primer and the R primer are represented as the positions in the nucleotide sequence shown in SEQ ID NO:1. The position of the probe 1 is represented as the position in the nucleotide sequence shown in SEQ ID NO:2.

Thereafter, the probe shown in Table 2, which has C at an end, was designed.

In Table 2, the position of the probe 1 is represented as the position in the nucleotide sequence shown in SEQ ID NO:2. P at the 3'-end indicates that the 3'-end is phosphorylated. Labeling with TAMRA was carried out according to a conventional method.

TABLE 2

| Name | Sequence | Position | SEQ ID NO: | mer | Tm (° C.) |
|---|---|---|---|---|---|
| VKORC1 F primer | 5'-ggaagtcaagcaagagaagacctg-3' | 47-70 | 3 | 24 | 57.58 |
| VKORC1 R primer | 5'-aatgctaggattataggcgtgag-3' | 121-99 | 4 | 23 | 55.36 |
| VKORC1 probe 1 | 5'-(TAMRA)-cattggccAggtgcggt-P-3' | 80-96 | 6 | 17 | 53.01 |

The melting temperature (Tm) was calculated according to the Nearest Neighbor method in http://www.m-neko.net/tm_calc/, with the settings of: primer conc., 250 nM; Na+ conc., 50 mM.

Using as a sample the human genome (human genome 1 or 2 in Table 4) purified from whole blood (100 copies/reaction liquid), PCR and Tm analysis were carried out using a fully automatic SNPs testing device (trade name: i-densy (trademark), manufactured by ARKRAY, Inc.). The conditions for the PCR and the Tm analysis were as shown in Table 5, and the composition of the PCR reaction liquid was as shown in Table 3.

The emission wavelength and the detection wavelength in the Tm analysis were 520 to 555 nm and 585 to 700 nm (TAMRA), respectively.

TABLE 3

In 50 μL of the PCR reaction liquid:

1 × reaction buffer
1.25 U Taq polymerase
1.5 mmol/L MgCl$_2$
0.2 mmol/L dNTP
0.5 μmol/L VKORC1 F primer (Table 2)
1 μmol/L VKORC1 R primer (Table 2)
0.2 μmol/L VKORC1 probe 1 (Table 2)

TABLE 4

|  | VKORC1-1639 | CYP2C9*3 |
|---|---|---|
| Human genome 1 | Ht(G/A) | Wt(A/A) |
| Human genome 2 | Mt(A/A) | Ht(A/C) |

Here, Ht represents a heterozygote, Wt represents the wild type, and Mt represents a variant.

TABLE 5

Conditions for PCR and Tm analysis

95° C., 60 sec
↓
(95° C., 1 sec.; 60° C., 15 sec.) × 50
↓
95° C., 1 sec.
↓
40° C., 60 sec.
↓
Tm (40° C.→75° C., 1° C./3 sec.)

As a result of the PCR and the Tm analysis using the probe shown in table 2, in terms of the human genome 1, peaks for TAMRA were observed at about 56° C. and about 64° C., and, in terms of the human genome 2, a peak for TAMRA was observed at about 64° C. (FIG. 1).

Example 2

Single, Whole Blood

The reaction was carried out in the same manner as in Example 1 except that whole blood was used as the sample.

Figure 2:
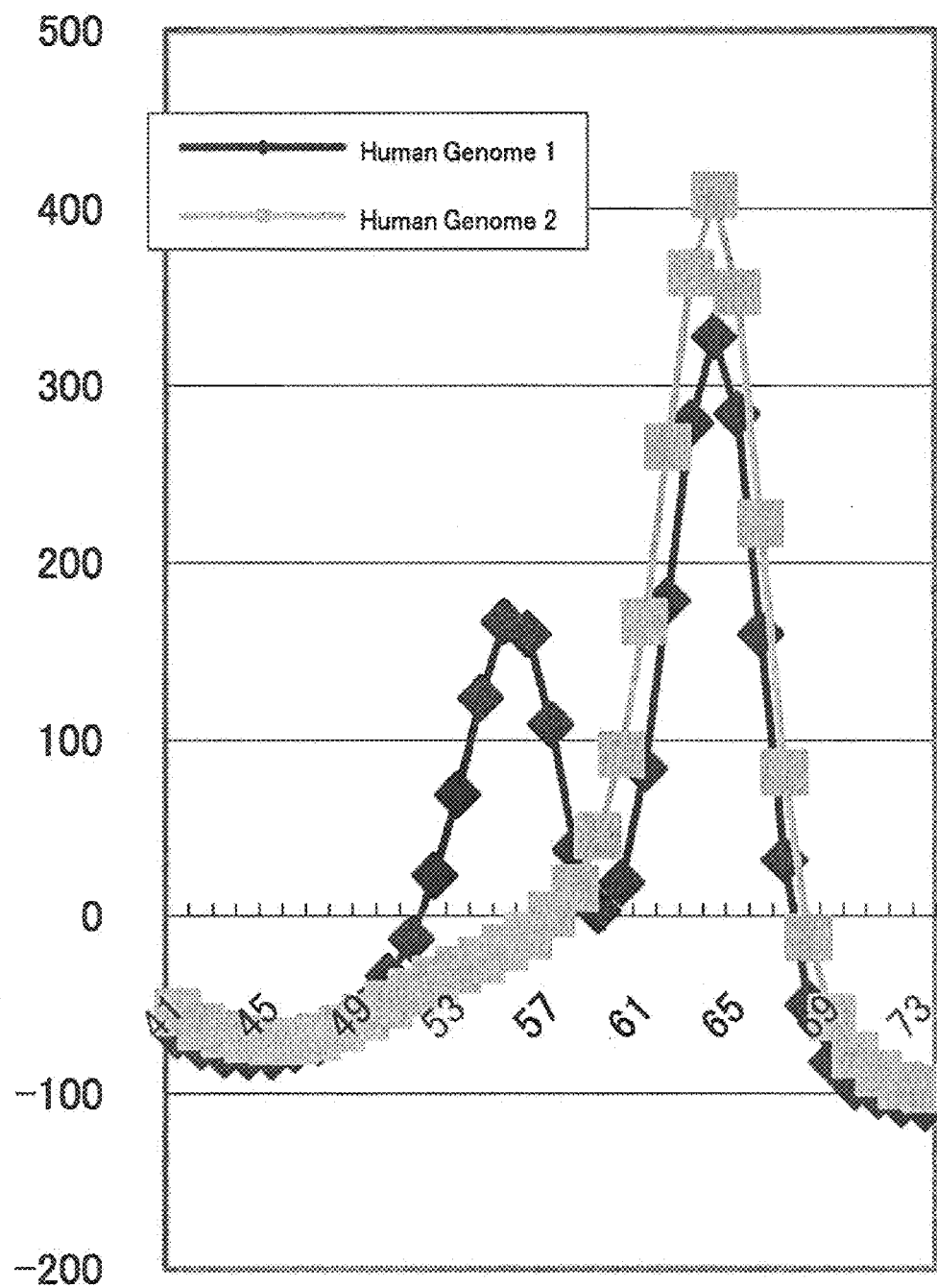
FIG. 2 shows the changes in the amount of change in the fluorescence intensity of TAMRA (VKORC1 probe 1) per unit time (d the amount of increase in the fluorescence intensity/t) in Tm analysis for the human genome 1 and the human genome 2 (whole blood) in Example 2. The ordinate indicates the amount of change in the fluorescence intensity per unit time (d the amount of increase in the fluorescence intensity/t), and the abscissa indicates the temperature (° C.).

As a result of the PCR and the Tm analysis using the probe shown in Table 2, in terms of the human genome 1, peaks for TAMRA were observed at about 56° C. and about 64° C., and, in terms of the human genome 2, a peak for TAMRA was observed at about 64° C. (FIG. 2), similarly to the results in Example 1.

Comparative Example

The reaction was carried out in the same manner as in Example 1 except that the PCR reaction liquid having the composition shown in Table 6 was used.

TABLE 6

In 50 μL of the PCR reaction liquid:

1 × reaction buffer
1.25 U Taq polymerase
1.5 mmol/L MgCl$_2$
0.2 mmol/L dNTP
1 μmol/L VKORC1 F primer (Table 2)
0.5 μmol/L VKORC1 R primer (Table 2)
0.2 μmol/L VKORC1 probe 2 (Table 7)

TABLE 7

| Name | Sequence | Position | SEQ ID NO: | mer | Tm (° C.) |
|---|---|---|---|---|---|
| VKORC1 probe 2 | 5'-(TAMRA)-caccTggccaatggtt-P-3' | 92-77 | 7 | 16 | 46.26 |

*The position of the probe 2 is represented as positions in the nucleotide sequence shown in SEQ ID NO: 2.

Figure 3:
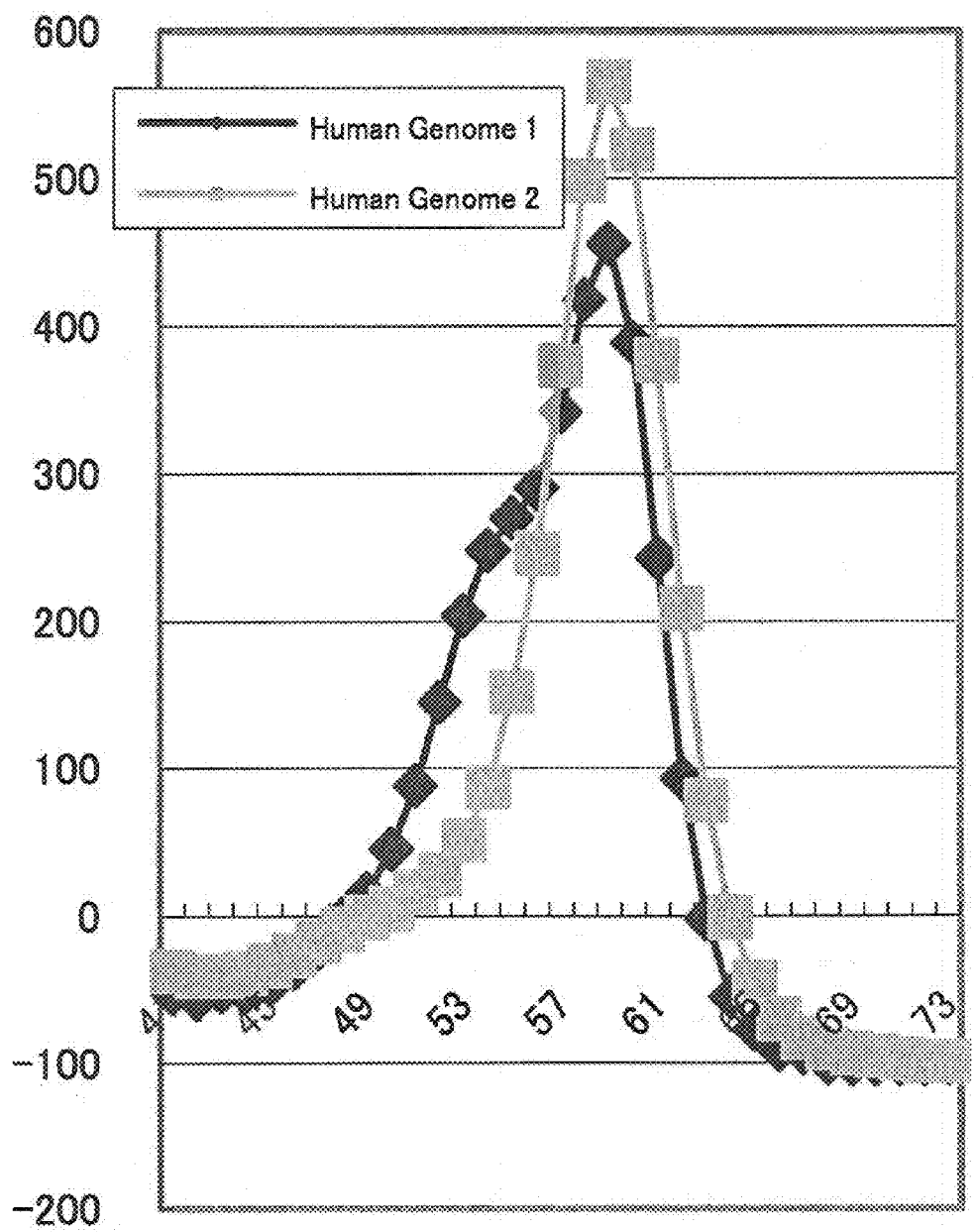
FIG. 3 shows the changes in the amount of change in the fluorescence intensity of TAMRA (VKORC1 probe 2) per unit time (d the amount of increase in the fluorescence intensity/t) in Tm analysis for the human genome 1 and the human genome 2 (purified genome) in Comparative Example. The ordinate indicates the amount of change in the fluorescence intensity per unit time (d the amount of increase in the fluorescence intensity/t), and the abscissa indicates the temperature (° C.).

As a result of the PCR and the Tm analysis using the probe shown in table 7, only a single peak for TAMRA was observed at about 59° C. in the both human genomes 1 and 2, and therefore it was impossible to distinguish between the heterozygote and the homozygote (FIG. 3). Thus, it is understood that the sequence of the probe cannot be arbitrary even in cases where C at the 5'- or 3'-end of the probe is fluorescently labeled, and that fluorescent labeling of C at position 80, similarly to the case of the probe shown in SEQ ID NO:6, is important.

From the results of Examples 1 and 2 and Comparative Example, change in the fluorescence intensity was found when the probe of SEQ ID NO:6 was used for detecting the polymorphism at position −1639 of the VKORC1 gene, which change could be analyzed by the Tm analysis. That is, in terms of this mutation, the human genome 1, which is heterozygotic, showed the two peaks at about 56° C. and about 64° C., while the human genome 2, which is a variant, showed only the single peak at about 64° C., suggesting that a unique change in the pattern of the amount of change in the fluorescence intensity exists. Further, from these results, it can be seen that the reaction using the wild-type human genome for detection of this mutation results in a single peak at about 56° C.

Therefore, by using the probe of SEQ ID NO:6, the polymorphism at position −1639 of the VKORC1 gene can be detected.

Example 3

Multiple, Purified Genome

The reaction was carried out in the same manner as in Example 1 except that the PCR reaction liquid having the composition shown in Table 8 was used.

The emission wavelength and the detection wavelength in the Tm analysis were 420 to 485 nm and 520 to 555 nm (BODIPY FL), respectively, or 520 to 555 nm and 585 to 700 nm (TAMRA), respectively.

TABLE 8

In 50 µL of the PCR reaction liquid:

1 × reaction buffer
1.25 U Taq polymerase
1.5 mmol/L MgCl$_2$
0.2 mmol/L dNTP
14% (v/v) Glycerol
0.5 µmol/L VKORC1 F primer (Table 2)
1 µmol/L VKORC1 R primer (Table 2)
0.4 µmol/L VKORC1 probe 1 (Table 2)
2 µmol/L CYP2C9*3 F primer (Table 9)
1 µmol/L CYP2C9*3 R primer (Table 9)
0.2 µmol/L CYP2C9*3 probe 1 (Table 9)

TABLE 9

As the CYP2C9*3 primers and probe, the followings were used.

| Name | Sequence | SEQ ID NO: | mer | Tm (° C.) |
|---|---|---|---|---|
| CYP2C9*3 F primer | 5'-cggagcccctgcatgcaa-3' | 8 | 18 | 57.04 |
| CYP2C9*3 R primer | 5'-aatgatactatgaatttggggacttcgaa-3' | 9 | 29 | 57.23 |
| CYP2C9*3 probe 1 | 5'-ggagaaggtcaaGgtatc-(BODIPY FL)-3' | 10 | 17 | 45.44 |

The above CYP2C9*3 probe 1 has the nucleotide sequence shown in SEQ ID NO:29 in WO2008/066163 and SEQ ID NO:45 in WO2008/117782.

Figure 4:
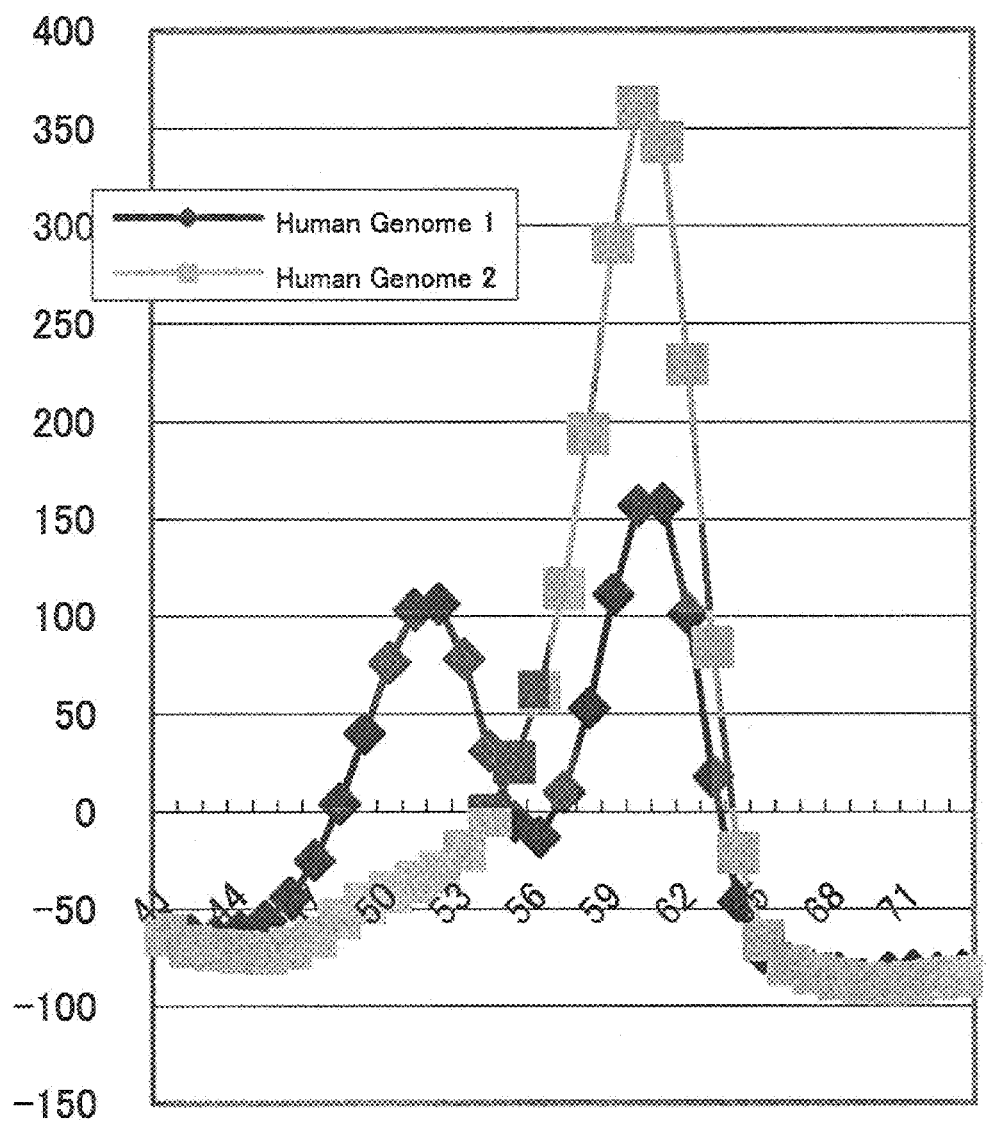
FIG. 4 shows the changes in the amount of change in the fluorescence intensity of TAMRA (VKORC1 probe 1) per unit time (d the amount of increase in the fluorescence intensity/t) in Tm analysis for the human genome 1 and the human genome 2 (purified genome) in Example 3. The ordinate indicates the amount of change in the fluorescence intensity per unit time (d the amount of increase in the fluorescence intensity/t), and the abscissa indicates the temperature (° C.).
Figure 5:
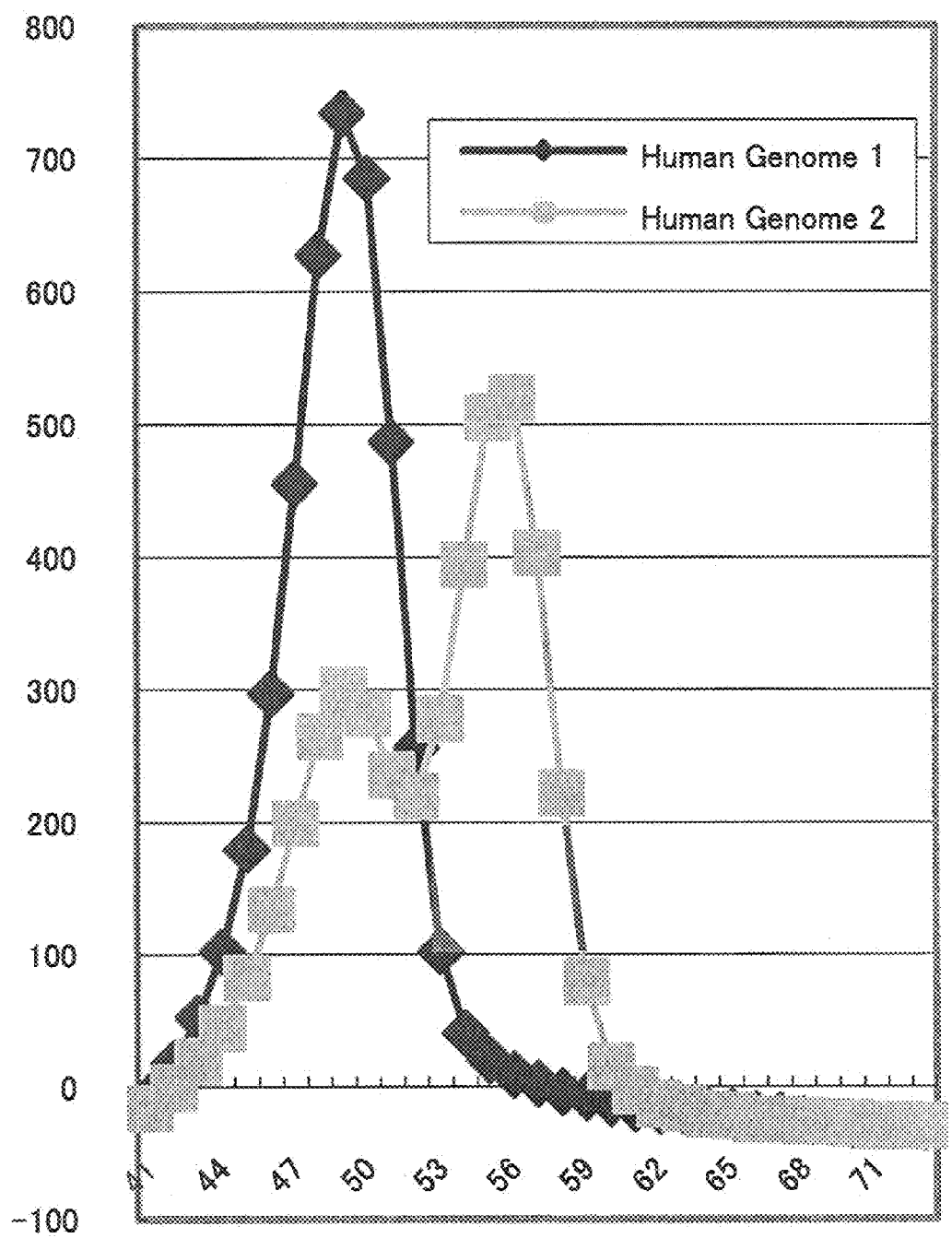
FIG. 5 shows the changes in the amount of change in the fluorescence intensity of BODIPY FL (CYP2C9*3 probe 1) per unit time (d the amount of increase in the fluorescence intensity/t) in Tm analysis for the human genome 1 and the human genome 2 (purified genome) in Example 3. The ordinate indicates the amount of change in the fluorescence intensity per unit time (d the amount of increase in the fluorescence intensity/t), and the abscissa indicates the temperature (° C.).

As a result of evaluation by fluorescence of TAMRA, in terms of the human genome 1, peaks for TAMRA were observed at about 52° C. and about 60° C., and, in terms of the human genome 2, a peak for TAMRA was observed at about 60° C. (FIG. 4). Further, as a result of evaluation by fluorescence of BODIPY FL, in terms of the human genome 1, a peak for BODIPY FL was observed at about 49° C., and, in terms of the human genome 2, peaks for BODIPY FL were observed at about 49° C. and about 56° C. (FIG. 5).

Example 4

Multiple, Whole Blood

The reaction was carried out in the same manner as in Example 3 except that whole blood was used as a sample. The whole blood was subjected to pretreatment as follows before use.

To 70 µl of the dilution liquid (1) described below, 10 µl of whole blood was added, and the resulting mixture was mixed well, followed by adding 10 µl of this mixture to 70 µl of the dilution liquid (2) described below. At 95° C., 17 µl of this mixture was heated for 10 minutes, to obtain 4 µl of pretreated whole blood, which was then used as a sample.

Dilution Liquid (1)
10 mM Tris-HCl (pH 8.0)
mM EDTA (pH 8.0)
0.3% (v/v) SDS
Dilution Liquid (2)
10 mM Tris-HCl (pH 8.0)
mM EDTA (pH 8.0)

Figure 6:
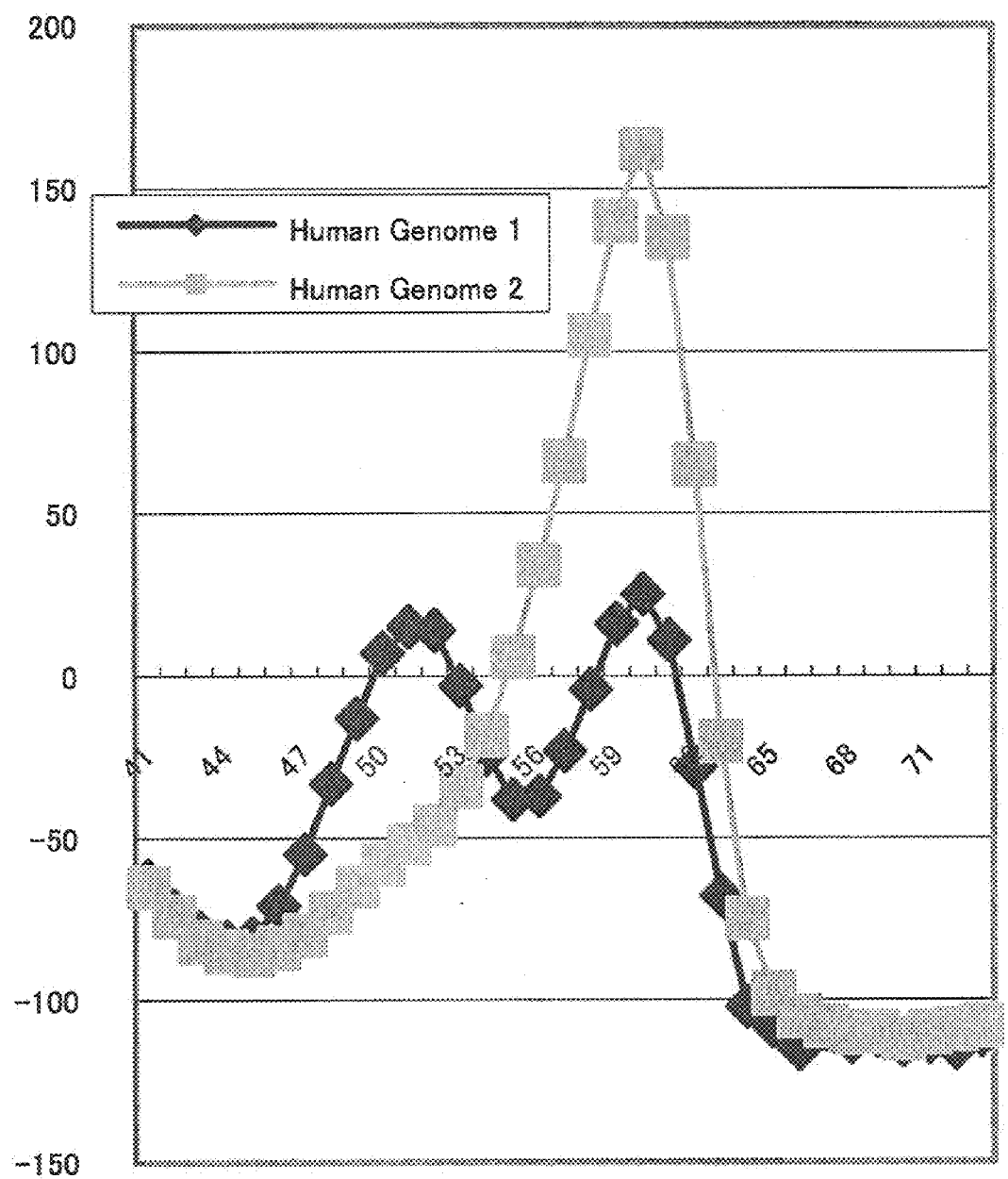
FIG. 6 shows the changes in the amount of change in the fluorescence intensity of TAMRA (VKORC1 probe 1) per unit time (d the amount of increase in the fluorescence intensity/t) in Tm analysis for the human genome 1 and the human genome 2 (whole blood) in Example 4. The ordinate indicates the amount of change in the fluorescence intensity per unit time (d the amount of increase in the fluorescence intensity/t), and the abscissa indicates the temperature (° C.).
Figure 7:
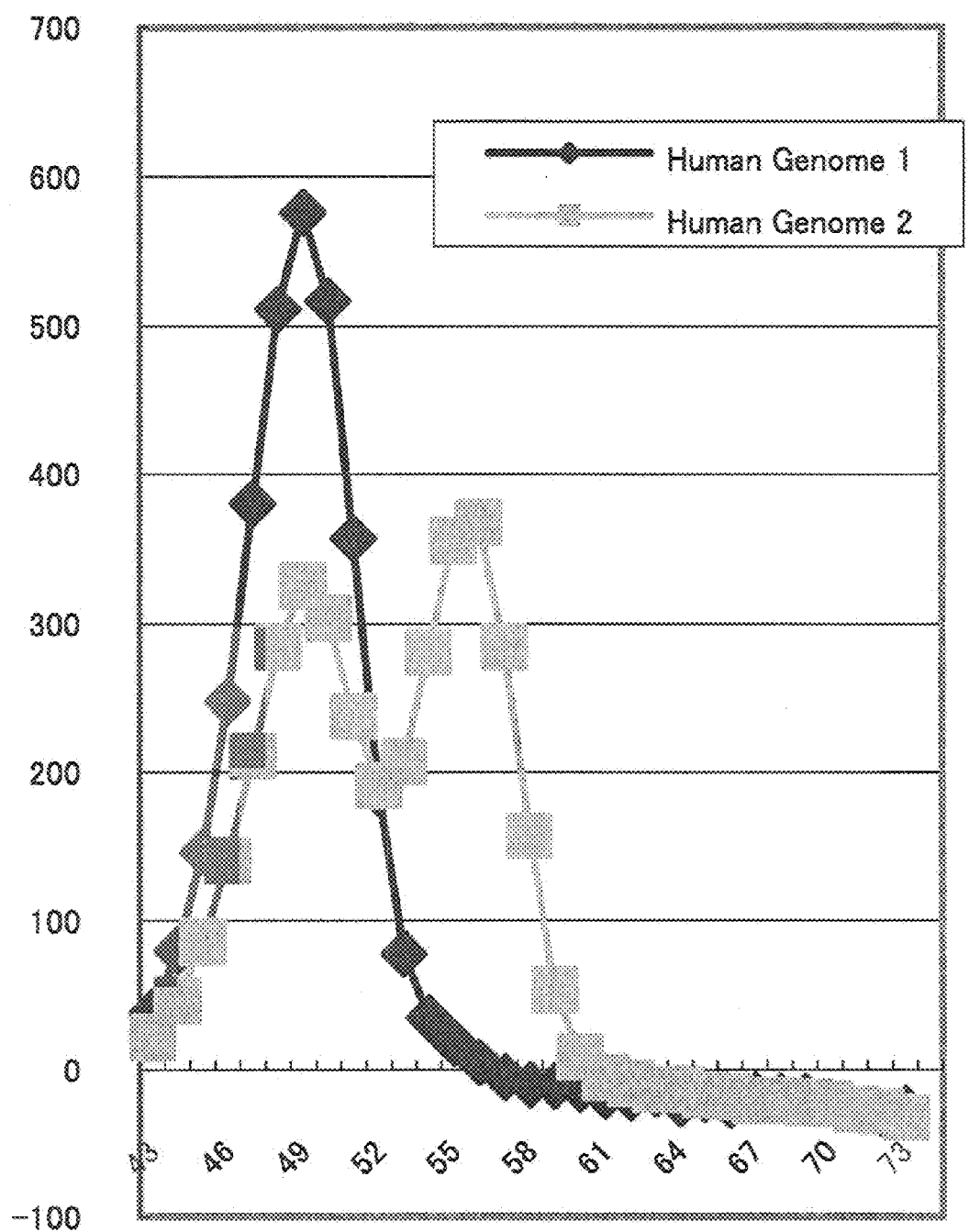
FIG. 7 shows the changes in the amount of change in the fluorescence intensity per unit time (d the amount of increase in the fluorescence intensity/t) in Tm analysis for the human genome 1 and the human genome 2 (whole blood) in Example 4. The ordinate indicates the amount of change in the fluorescence intensity of BODIPY FL (CYP2C9*3 probe 1) per unit time (d the amount of increase in the fluorescence intensity/t), and the abscissa indicates the temperature (° C.).

As a result of evaluation by fluorescence of TAMRA, in terms of the human genome 1, peaks for TAMRA were observed at about 51° C. and about 60° C., and, in terms of the human genome 2, a peak for TAMRA was observed at about 60° C. (FIG. 6), similarly to the results in Example 3. Further, as a result of evaluation by fluorescence of BODIPY FL, in terms of the human genome 1, a peak for BODIPY FL was observed at about 49° C., and, in terms of the human genome 2, peaks for BODIPY FL were observed at about 49° C. and about 56° C. (FIG. 7).

From the results of Examples 3 and 4, change in the fluorescence intensity was found when the probe of SEQ ID NO:6 was used for detecting the polymorphism at position −1639 of the VKORC1 gene, which change could be analyzed by the Tm analysis. That is, in terms of this mutation, the human genome 1, which is heterozygotic, showed the two peaks at about 52° C. and about 60° C., while the human genome 2, which is a variant, showed only the single peak at about 60° C., suggesting that a unique change in the pattern of the amount of change in the fluorescence intensity exists. Further, from these results, it can be seen that the reaction using the wild-type human genome for detection of this mutation results in a single peak at about 52° C.

Further, also in terms of the polymorphism at the CYP2C9*3 mutation site, change in the fluorescence intensity which can be analyzed by the Tm analysis was found. That is, in terms of this mutation, the human genome 1, which is the wild type, showed only a single peak at about 49° C., while the human genome 2, which is heterozygotic, showed the two peaks at about 49° C. and about 56° C., suggesting that a unique change in the pattern of the amount of change in the fluorescence intensity exists. Further, from these results, it can be seen that the reaction using the variant-type human genome for detection of this mutation results in a single peak at about 56° C.

Thus, by using the probes shown in SEQ ID NOs:6 and 10 at the same time, the polymorphism at position −1639 of the VKORC1 gene and the polymorphism at the CYP2C9*3 mutation site can be detected at the same time.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A probe consisting of the nucleotide sequence of SEQ ID NO: 6 where position 1 is labeled with a fluorescent dye.

2. A method for detecting a polymorphism in the VKORC1 gene, which method comprises using the probe according to claim 1.

3. The method according to claim 2, said method comprising:
(I) bringing the probe into contact with a single-stranded nucleic acid in a sample, to allow hybridization of said fluorescently labeled oligonucleotide with said single-stranded nucleic acid;
(II) changing the temperature of the sample containing the hybrid to dissociate the hybrid, and measuring fluctuation of the fluorescence signal due to the dissociation of the hybrid;
(III) determining the Tm value, which is the dissociation temperature of the hybrid, based on the fluctuation of said signal; and
(IV) determining the presence of a polymorphism or the abundance ratios of nucleic acids having polymorphisms in the VKORC1 gene based on said Tm value.

4. The method according to claim 3, said method further comprising amplification of nucleic acid before said Step (I) or at the same time with said Step (I).

5. A kit for detecting a polymorphism, said kit comprising the probe according to claim 1.

6. The kit according to claim 5, further comprising at least one primer a for amplification of a region in the nucleotide sequence shown in SEQ ID NO:1, said region comprising a sequence with which said oligonucleotide hybridizes.

7. The kit according to claim 6, wherein said primers are the primers shown in SEQ ID NOs:3 and 4.

8. The kit according to claim 6, further comprising the primers shown in SEQ ID NOs:8 and 9 and the probe shown in SEQ ID NO:10.

* * * * *